United States Patent [19]
Alt

[11] Patent Number: 5,403,355
[45] Date of Patent: Apr. 4, 1995

[54] IMPLANTABLE MEDICAL INTERVENTIONAL DEVICE WITH ATRIAL DYSRHYTHMIA THERAPY FOR TACHYCARDIA

[75] Inventor: Eckhard Alt, Ottobrunn, Germany

[73] Assignee: Intermedics, Inc., Angleton, Tex.

[21] Appl. No.: 279,947

[22] Filed: Jul. 25, 1994

Related U.S. Application Data

[60] Division of Ser. No. 916,588, Jul. 20, 1992, which is a continuation-in-part of Ser. No. 863,092, Apr. 3, 1992, Pat. No. 5,342,404.

[51] Int. Cl.6 .............................................. A61N 1/368
[52] U.S. Cl. ............................................................ 607/9
[58] Field of Search ............................... 607/4, 6, 9, 19

[56] References Cited

U.S. PATENT DOCUMENTS 4,998,974 3/1991 Aker ......................................... 607/4
5,014,698 5/1991 Cohen ....................................... 607/4

Primary Examiner—William E. Kamm
Attorney, Agent, or Firm—O'Connor, Cavanagh, Anderson, Westover, Killingsworth & Beshears

[57] ABSTRACT

An implantable medical interventional device for delivering electrical therapies to the heart of an implant patient to treat pathologic ventricular tachycardia. The device includes a first sensor for developing a signal indicative of the patient's ventricular ECG status, and a second sensor for developing a signal indicative of the patient's atrial ECG status. Criteria are established to distinguish physiologic tachycardia and pathologic tachycardia in the ventricles by an evaluation of the signal indicative of ventricular ECG status, and an appropriate is therapy is delivered if the evaluation indicates a pathologic tachycardia in progress. The therapy delivery is limited to an atrial response if the signal developed by the second sensor indicates atrial fibrillation or other atrial dysrhythmia, and is appropriate to that particular dysrhythmia. The evaluation is performed by comparing the signals indicative of atrial and ventricular ECG status to discriminate primary ventricular tachycardias from secondary ventricular tachycardias of primary atrial origin. The therapy is delivered in a tiered regimen and, in response to the discrimination of primary and secondary ventricular tachycardia, is adjusted accordingly. The tiered therapy regimen may include a therapy of solely atrial defibrillation. A non-ECG sensor may additionally be used to sense a physiological parameter indicative of patient activity. In that case, in response to detection of ventricular tachycardia by the first sensor, detection of atrial tachycardia by the second sensor, and indication of patient resting condition or low level activity by the non-ECG sensor, a ventricular tachycardia is treated as pathologic atrial tachycardia, and atrail therapy is applied without any therapy to the ventricle.

16 Claims, 3 Drawing Sheets

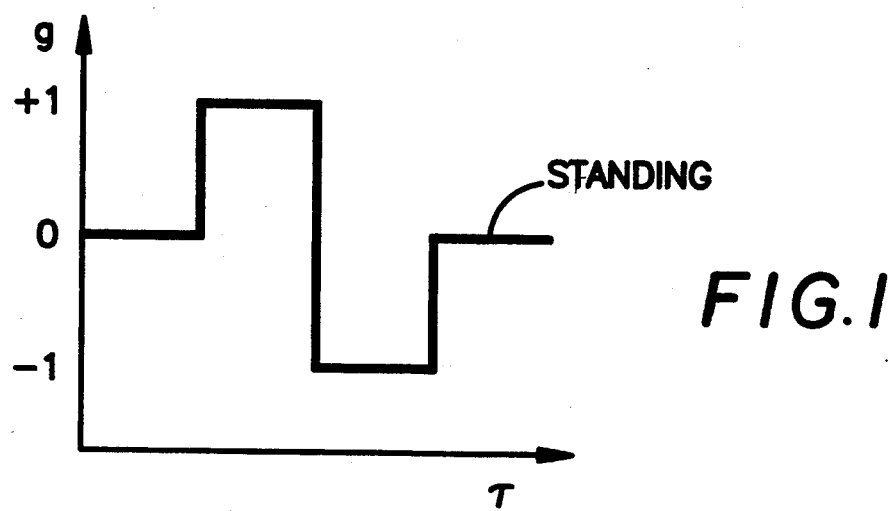
FIG.1
FIG.2
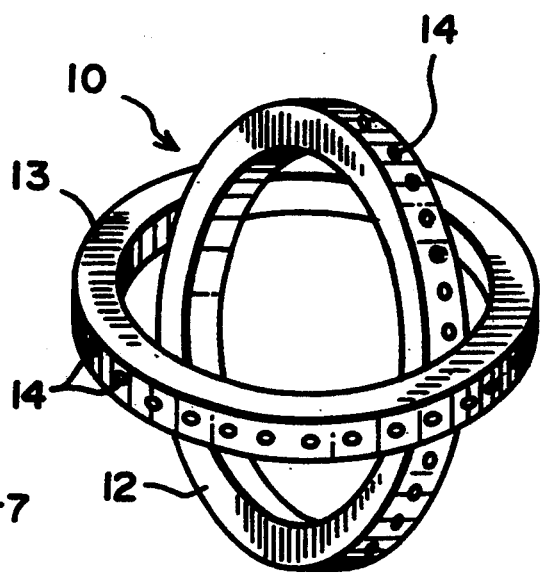
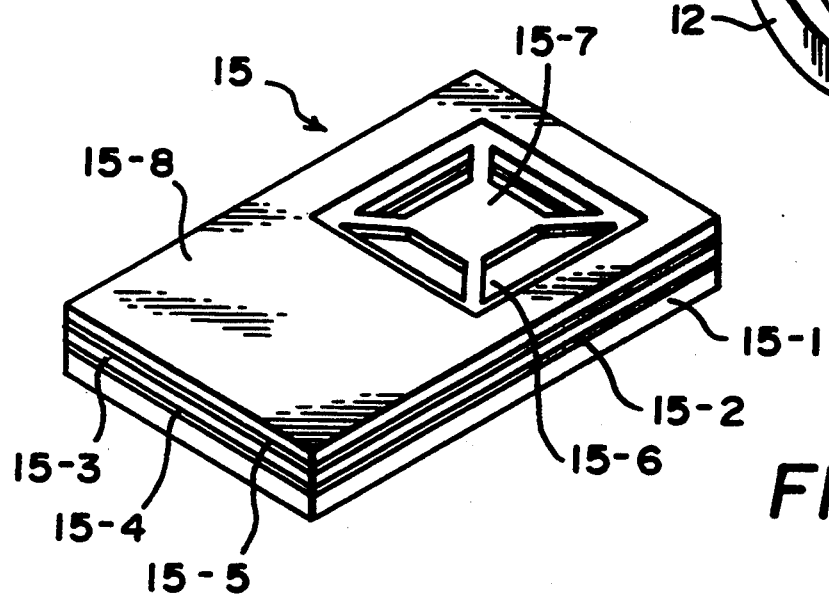
FIG.3

IMPLANTABLE MEDICAL INTERVENTIONAL DEVICE WITH ATRIAL DYSRHYTHMIA THERAPY FOR TACHYCARDIA

CROSS-REFERENCE TO RELATED APPLICATION

This application is a division of co-pending U.S. patent application Ser. No. 07/916,588, filed Jul. 20, 1992, which is a continuation-in-part of application Ser. No. 07/863,092, filed Apr. 3, 1992, now U.S. Pat. No. 5,342,404.

BACKGROUND OF THE INVENTION

The present invention relates generally to implantable medical devices, and more particularly to an implantable interventional device such as an antitachycardia pacemaker, a cardioverter, a defibrillator, or a device having a combination of such functions, adapted to deliver electric impulse or shock therapies to the patient's heart upon detection of a ventricular tachycardia (VT) or ventricular fibrillation (VF). More particularly, the invention relates to improvements in apparatus and methods for detecting and distinguishing pathological tachycardias from physiological tachycardias and for establishing the type and timing of the delivery of the appropriate therapy upon detection of pathologic VT or VF.

Sinus heart rates in normal healthy adults may range upward to 160 beats per minute (bpm) during physical activity or exercise, or even when the individual is experiencing emotional stress or excitement. Rates up to even 200 bpm may be experienced during strenuous exercise. Such elevated rates occurring in these circumstances stances are a normal reaction by the organism and are termed physiological tachycardias. The heart rate gradually, perhaps even quickly, decreases to the normal resting rate when the factors leading to the increase d rate have ceased.

In contrast, random or spontaneous elevation of the heart rate to such levels for no apparent reason constitutes pathological tachycardia attributable to cardiovascular disease, and requires intervention with appropriate medical therapy. In general, pathological tachycardia hi the atrium is tolerated because the excitable A-V junction tissue (between the atrium and ventricle) has a longer refractory period and slower conductivity than myocardial tissue, so that the rapid atrial contractions typically fail to induce correspondingly rapid ventricular contractions, allowing cardiac output to remain relatively strong with a ventricular rhythm nearer the sinus rate.

On the other hand, pathological tachycardia in the ventricles, the main pumping chambers of the heart, is not well tolerated. The rapid contractions permit only partial filling of the chambers with oxygenated blood and result in diminished cardiac output. Moreover, ventricular tachycardia (VT) tends to accelerate spontaneously to ventricular fibrillation (VF), in which synchronous contractions of the tissue cease and the myocardial contractions become random and uncoordinated. The resulting loss of cardiac output requires immediate intervention to defibrillate, failing which death will ensue. Generally, VF occurs only after VT; only rarely is VF not precipitated by a pathological tachycardia.

Although atrial tachycardia (AT) is relatively common, patients who are symptomatic or at high risk may be treated with drugs, antitachycardia pacemakers, or in some extreme cases, suck as where the AT tends to escalate to atrial fibrillation (AF), by performing a surgical A-V block and a ventricular pacemaker implant. Antitachycardia pacemakers, which often are also prescribed for patients suffering VT, are usually adapted to overstimulate the heart by applying pulses at a programmed rapid rate to suppress the ectopic activity that leads to premature atrial or ventricular contractions. Pulses of relatively low energy content may suffice to break the tachycardia and restore normal heart rate. The term "cardioversion" usually implies delivery of higher energy electrical shocks to the heart to break the tachycardia. Unfortunately, both antitachycardia and cardioversion therapies which are used for terminating VT can contribute to acceleration into VF.

Defibrillators are employed to apply one or more high energy electrical shocks to the heart in an effort to overwhelm the uncoordinated contractions of the various sections of the myocardial tissue and reestablish organized spreading of action potentials from cell to cell, thereby to restore synchronized contractions of the ventricles. Automatic implantable defibrillators were described in the literature at least as early as 1970, in separate articles of M. Mirowski et al. and J. Schuder et al. Innovations since proposed have included automatic implantable defibrillators which perform multiple functions of antitachycardia, cardioversion and defibrillation, and where appropriate, demand bradycardia pacing. In general, the desire is to use one or more pulse sequence or low level shock therapies for breaking VT before it spontaneously progresses into VF, and, if that fails or if VF occurs without preliminary pathologic tachycardia, to resort to a high energy defibrillating shock.

Typically, the shocks are delivered from one or more output storage capacitors of sufficient capacity in the implanted device. Energy requirements generally range from as little as 0.05 joule to up to 10 joules for cardioversion, and from 5 joules to about 40 joules for defibrillation, depending on the patient, the nature of the electrical waveform applied, and the efficiency of the energy transfer through the electrodes and into the heart tissue. The capacitors must be charged to the level appropriate for the therapy when the dysfunction or dysrhythmia is detected, so that the energy required for the shock will be rapidly available far delivery. Multiphasic shocks have been found quite effective. It is customary to provide a preset delay between successive shocks, and to inhibit further shocks when return to normal rhythm is detected.

As used in this specification, the terminology "shock" or "shocks" may include any pulse-type waveform, whether single phase or multiphase, which is delivered as antitachycardia, cardioverting or defibrillating therapy to a patient's heart in an effort to break, interrupt or terminate pathologic tachycardia or fibrillation and return the pumping action of the heart to a rate in the normal range; and "interventional device" includes any antitachycardia pacemaker, cardioverter, defibrillator or other device or combination thereof (which may include the function of conventional bradycardia pacing) which is adapted to be implanted or otherwise worn by a human or animal subject for the purpose of intervening to deliver shocks to the heart in response to detection of an abnormally rapid heart rate. The waveform is not limited to any particular energy content or range of energy content, and indeed, the therapy may include burst stimulation or other conventional techniques for applying stimulation pulses (such as for rapid pacing) to break a VT.

Proper operation of implantable antitachycardia pacemakers, cardioverters, defibrillators and similar medical devices necessitates proper timing of delivery of the therapy, including timing of charging and firing of shock-producing output capacitors. It is essential, first, that the device have the capability to distinguish physiological tachycardias from pathological tachycardias to assure that occurrence of the former will not be wrongly identified as the latter with the result that the patient is subjected to a shock when he or she is merely exercising, for example. Incapability to distinguish can mean, at the very least, that the capacitors are needlessly charged, and worse, that they are inappropriately discharged into the heart, with consequences ranging from painful shock and possible loss of consciousness to repetitive shocks.

In copending U.S. patent application Ser. No. 07/863,092 filed Apr. 3, 1992, ("the '092 application"), of which this application is a continuation-in-part, and which is incorporated herein by reference, physiological and pathological tachycardias are distinguished by resort to the use of two independent sensors, one of which detects electrocardiogram (ECG) or intrinsic electrical heart activity and the other, physical exercise by sensing activity. The latter sensor may be termed a complementary sensor, which, in the preferred embodiment of the invention disclosed in that application, is an accelerometer for detecting patient activity directly, but which instead might be an indirect sensor of physical exercise of the patient, such as blood pressure, blood oxygen content, minute ventilation, central venous temperature, pulse rate, or blood flow detector. Concurrent detection of patient cardiac activity (ECG) as well as physical activity provides improved discrimination between physiologic and pathologic tachycardias, particularly in an overlap range of heart rates from about 130 to about 180 beats per minute (bpm). This range presents especially serious problems when ECG detection alone is used and/or the patient may be experiencing either a fast physiological tachycardia or a relatively slow pathological VT.

For example, the ECG signal may indicate a VT of 150 bpm which is in the range of both pathologic and physiologic tachycardia for a particular patient, but if the activity status sensor (e.g., accelerometer) detects physical activity, the device would be inhibited from delivering antitachycardia treatment. On the other hand, the ECG may demonstrate VT or VF at a time when the activity status sensor indicates no movement of the patient, leading to the decision to trigger prompt therapy. The decision, therefore, is a reasoned one and is made automatically, and in the case of origin of a tachycardia, discriminates between physiologic and non-physiologic.

An implantable medical interventional device utilizing the complementary sensors may be programmed to respond to sensing an ECG signal indicative of possible slow VT, coupled with confirmation of physical inactivity of the patient by the other sensor, by stimulating the heart with low energy shocks to break the VT before it accelerates into VF. Alternatively, a more liberal programming philosophy may be followed in which slow tachycardia and lack of physical activity of the patient merely define an alert condition of the device in which the capacitors are charged to the proper energy level, in anticipation of the possibility that a more dramatic situation may develop. If delivery of an antitachycardia or defibrillating shock is subsequently determined to be warranted, precious tinge will not have been lost waiting for the output storage capacitors of the device to be charged.

The use of two complementary sensors serves not only to control charging and firing of the implantable interventional device for treatment of tachycardias and fibrillation, but to better evaluate the probability of success of interventional measures. Since VT may be broken by lower energy shocks than those needed to terminate VF, a considerable energy saving is achieved which helps to reduce the size of the battery and, consequently, of the implanted device itself, or to increase its lifetime with the same battery capacity, either of which is important to the development of self-powered implanted devices.

Numerous conventional electrical waveform therapies or therapy protocols may be programmed into the interventional device for selective application to the heart upon detection of an applicable cardiac event by the complementary sensors. For example, these may include single stimulating pulses, stimulating pulse sequences, stimulating pulse trains of variable repetition frequency, one or more bursts of stimulating pulses, and single phase or multiple phase shocks of variable energy content generally greater than the energy content of the pulses in the other protocols which are utilized for treatment. In general, the therapy is applied in successively more stringent protocols until it is successful to break the VT or VF. This is termed a "tiered" therapy.

Both the degree of difficulty to defibrillate and the likelihood of failure increase with the length of time that the patient is in fibrillation. It is crucial to reduce the time interval from onset of fibrillation to delivery of the initial shock to a minimum, to reduce the energy required to defibrillate the heart and to increase the opportunity to successfully resuscitate the patient. As pointed out above, it is considerably easier to interrupt a VT, which may require delivery of only one joule of electrical energy, than to terminate VF with the potential requirement of 15 joules or more in each shock. Correspondingly, resuscitation is much more achievable with a patient who has been in fibrillation for only a few seconds than if the attack has continued for several minutes. Prompt treatment is also important for the patient experiencing either VT or VF and fighting against loss of consciousness. An excessive interval from onset to delivery of therapy, e.g., ten to thirty seconds, may cause the patient to hint, whereas earlier intervention might well have allowed the circulatory system to compensate for the fast heart rate without the loss of consciousness.

This type of dual sensing helps the implanted programmable microprocessor-based interventional device to better interpret and distinguish tachycardias than the ECG criteria which typically has been used in prior art devices, such as heart rate, morphology of the ECG, sudden onset, rate stability, etc. At least in part this is because the activity status sensor is complementary, providing additional information concerning the cardiac event under scrutiny, rather than merely pan of the ECG criteria. As noted in the '092 application, improved discrimination is especially pronounced in the borderline region from 130 bpm to 180 bpm, thereby better avoiding needless, painful and debilitating shocking of the heart.

It is a principal object of the present invention to provide improvements in techniques for recognizing abnormal tachycardias, over the prior art and even that disclosed in the '092 application, particularly in the overlap or borderline region where pathological tachycardias had been virtually indistinguishable from physiological tachycardias.

SUMMARY OF THE INVENTION

The present invention, in one of its principal aspects, takes advantage of the detection capabilities of the complementary sensor, such as an accelerometer, to modify the rate criterion which is used for pathological tachycardia recognition. If the accelerometer indicates the patient is at rest, the criterion for deciding that a pathological tachycardia is in progress is set at a rate of 130 bpm, for example; on the other hand, if the accelerometer indicates patient activity, the tachycardia rate criterion is shifted to 170 bpm.

This is vastly different from the technique used in the prior art. The problem that exists with the prior art devices is that they invariably employ a single fixed rate which represents a compromise between the heart rate the particular patient might exhibit during exercise and the rate thought to be indicative a pathological tachycardia. The overlap makes it very difficult to accurately determine whether the event of interest warrants intervention because some individuals may have a pathological tachycardia rate of 140 bpm, or even 130 bpm, and yet may also exhibit an exercise tachycardia rate of 140 bpm, or even 150 bpm. If the prior art rate criterion for such a patient were set at 140, the patient would receive a defibrillating shock from the implanted automatic defibrillator when he or she is merely exercising.

Although currently available cardioverters/defibrillators are adapted to operate on the principle of applying a whole bundle of distinct ECG criteria to recognize a tachycardia (pathological), including sudden rate change, rate stability, probability density function, and so forth, the principal criterion used is purely rate. If any rate above 160 bpm is considered to be pathological, these devices can fail to recognize a tachycardia for which intervention is needed where the rate in question is anywhere below 160 bpm.

With the present invention, the intervention rate is easily adjusted or shifted according to the status of patient activity or exercise, which is to say, the rate criterion for tachycardia recognition applied to the ECG signal is changed simply and effectively depending upon the output or merely the status of the complementary sensor.

The present invention modifies the criteria to recognize a pathologic tachycardia by assessing the ECG signal according to the output signal of the activity status sensor. That is, if the output signal of the activity status sensor is not present or is quite low, indicative of rest, the pathologic tachycardia recognition ECG rate criterion is preprogrammed to be correspondingly low (e.g., perhaps a heart rate of 150 bpm); but when the activity sensor output increases, indicative that the patient is undergoing exercise, the rate criterion is programmed to shift automatically to a higher value (increasing to, perhaps, 150 or even 170 bpm, depending on the particular patient). In the preferred embodiment, this threshold rate moves up or down according to the status of the output signal of the accelerometer. This provides information not only about the pathological tachycardia rate but also its morphology.

As in the device of the '092 application, the implantable medical interventional device of the present invention responds to detection of cardiac activity of the patient indicative of the abnormal VT or of VF by selectively applying to the patient's heart a conventionally selected sequence of different electrical waveforms (e.g., single pulse, dual pulses, pulse trains or bursts, biphasic or triphasic shocks, etc.). Each time a new waveform is applied or repeated during the course of treatment of an ongoing VT or VF, the ECG is monitored to determine whether that treatment was successful, and, if not, the therapy is continued. Otherwise, it is terminated. A control means which is a function of the microprocessor software, or an independent subsystem of the overall electronics system package of the device, selects the appropriate electrical therapy for the sensed abnormal tachyrhythmia according to the programmed response to the recognized event. The device further includes an evaluation means operatively associated with the control means for modifying or adjusting the ECG criteria, and specifically the tachycardia recognition rate or threshold rate by which normal tachycardias are discriminated from abnormal tachycardias, according to the status of the activity signal, i.e., whether it indicates inactivity or activity, and in the latter case, the general extent or level of the activity.

The threshold rate is shifted to higher values with commencement or increases of physical activity by the patient and shifted to lower values with decreases or cessation of the physical activity. The electrical therapy may be tiered so that the shift applies to entire different zones of ECG recognition rates and to the related therapeutic consequences of a tachycardia recognized in one of the zones, such as increasingly aggressive therapy protocols applied with either continuation or acceleration of the tachycardia and the initial therapy selected for a protocol.

Therefore, it is another object of the invention to provide a simple and effective technique for identifying tachycardias arising from heart or cardiovascular disease, for distinguishing them from naturally occurring elevated heart rates attributable to stress including physical exercise by the application of an ECG rate criterion which is controlled by a non-ECG sensor output, and for shifting the ECG rate criterion in response to a material change in the non-ECG sensor output.

According to another significant aspect of the present invention, an atrial bipolar electrode is used to check the status of the atrial ECG to detect atrial tachycardia. The purpose is to avoid one of the problems associated with conventional implantable defibrillators, viz., that of inappropriate firing (i.e., discharge of the capacitors to deliver the shock(s) to the heart). This may occur, for example, where the tachycardia recognition criteria is set within a zone encompassing a ventricular rate such as 130 to 140 bpm, and the patient experiences atrial fibrillation with that ventricular rate. The complementary activity sensor used in the apparatus of the invention may not be entirely helpful in these circumstances, because it could be indicating at that time that the patient is resting or undergoing mild activity, if that is the case, with a consequent lowered tachycardia recognition rate. Hence, if the status of the atrial ECG were not being detected, the patient would receive a shock in the region of the ventricles. By use of an atrial bipolar electrode for such sensing, the device of the invention avoids the delivery of such a shock.

According to another, associated feature of the invention, detection of atrial fibrillation in this way is used to trigger the delivery of low energy shocks such as in the energy range from 0.25 to 1.0 joule from the implanted device to the atrial chambers, and thereby defibrillate the atrium alone. A tiered therapy regimen may be used here as well, to provide an improved protocol for treating atrial dysrhythmias such as atrial flutter, atrial tachycardia or atrial fibrillation.

Therefore, yet another object of the invention is to avoid inappropriate firing of the implanted defibrillator into the ventricles when the patient is actually experiencing atrial fibrillation, by detecting the status of the atrial ECG.

A further object of the invention is to defibrillate the atrium alone upon such detection of atrial fibrillation, and to employ a tiered therapy regimen to treat atrial dysrhythmias.

According to still another aspect of the invention, the R-R interval—the coupling interval between beats—is detected and the ventricular ECG signals are analyzed to determine whether the tachycardia is regular or a variation in the R-R intervals. A variation in the R-R coupling interval is an indication that atrial dysrhythmia is occurring. It is desirable in such a situation to seek to terminate the atrial dysrhythmia, which will eliminate the VT because the atrial problem is primary and the VT is only secondary—rather than to attempt to terminate the VT directly. It follows that in this case it would be undesirable to modify the tachycardia recognition rate. Such modification is used specifically for detection of VT under conditions indicative of apparent exercise by the patient, which clearly is not occurring in this case. Accordingly, the modification response to the activity sensor output is disabled when a variation in the R-R interval is detected while a VT is occurring.

Hence, it is still another object of the present invention to determine whether a detected VT is primary or secondary by observing the nature of the R-R interval, and specifically to direct the implanted cardioverter/defibrillator to apply a therapy to terminate atrial dysrhythmia rather than to apply a therapy directly toward breaking the ventricular tachycardia.

A further object of the invention is to disable the VT recognition criteria modification-producing circuitry of the tachycardia detector of an implantable defibrillator when atrial dysrhythmia is occurring, by performing the disabling function when a varying R-R interval, in contrast to a regular R-R interval, is detected in the patient's ECG.

BRIEF DESCRIPTION OF THE DRAWINGS

The above and other objects, aspects, features and attendant advantages of the present invention will become apparent from a consideration of the following detailed description of a presently preferred embodiment and method, taken in conjunction with the accompanying drawings, in which:

FIG. 1 is a graph illustrating readouts measured in g versus time from a non-ECG sensor implanted in a patient;

FIG. 2 is a perspective view of a non-ECG sensor in the form of an activity status sensor (accelerometer) comprised of a pair of mercury ball sensors in fixed orthogonal orientation as implanted in a patient;

FIGS. 3 is another embodiment of an accelerometer, fabricated in an integrated or hybrid electronic circuit;

DESCRIPTION OF THE PREFERRED EMBODIMENT AND METHOD

Figure 4:
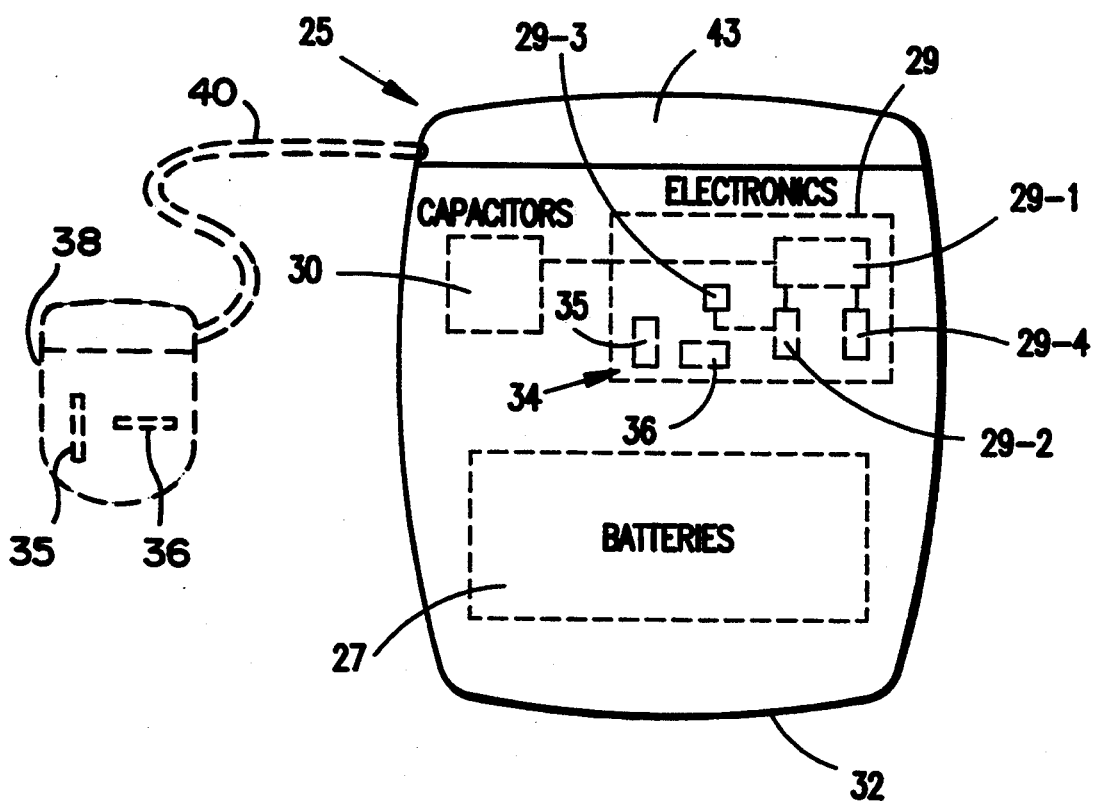
FIG. 4 is a simplified diagram of an implantable medical interventional device with activity status sensor(s) located within the device housing, and, in phantom, in an alternative arrangement in which the sensor is housed in its own separate case and connected by an electrical lead to a connector on the device housing.

The implantable medical interventional device to be described utilizes a direct sensor of electrical cardiac activity such as an ECG sensor, and an activity status sensor adapted to detect the position and movements of the patient, in the form of an accelerometer or other electromechanical converter, which may be calibrated for both static and dynamic outputs. The static output will depend upon the physical position or posture of the implant patient when inactive (e.g., at rest, or in a state of collapse). Assume that the activity status sensor is oriented vertically when implanted, and in that position produces a zero g (i.e., unit of gravity) output. The sensor produces a +1 g output in one aspect of its horizontal orientation, (i.e., one major side down), and produces a −1 g output in the opposite aspect of horizontal orientation (the other major side down).

In the example of FIG. 1, the activity status sensor provides a zero reading when the patient is standing during a first time interval, a +1 when the patient is supine during a second time interval, and a −1 when the patient is prone during a third interval. This chart is not intended to show the response of the activity status sensor to changes in position, such as in the; period between the first and second intervals, but only that different readouts or signals are produced by the sensor upon detection of different static positions of the patient.

The particular outputs may be modified by calibrating the sensor for slight deviations of orientation relative to these three positions. If the patient were lying on a side, the sensor reading would not be +1 or −1, but a non-zero value. By calibrating the electrical output of the sensor circuit after implantation, or by autocalibration of the device itself, the orientation of the sensor in any position of the patient will be known from the readout. By employing a second such activity status sensor with a 90° orientation relative to the first sensor, each sensor recognizes two of the three mutually orthogonal axes (X-Y-Z) in three dimensional space, and both together detect a full three axis orientation, to provide a combined reading uniquely identifying the patient's position. Thus, the sensor may be used to detect static or stable (i.e., non-moving) position of the patient, and patient activity constituting dynamic movements of the patient, such as a momentary change of position or continuing movements such as walking, dancing, bicycling, and so forth.

The activity status sensor may be of the mercury ball type described in U.S. Pat. No. 4,846,195. If a single such sensor were used as an X-Y axes (two dimensional) detector, it would not uniquely identify patient position. Two such sensors with fixed orthogonal orientation will provide combined detection of all three axes (X-Y-Z) of position or direction of movement. Referring to FIG. 2, sensor 10 includes a pair of mercury ball sensors 12 and 13 coupled together at an angle of 90 degrees. This fixed orientation of the two assures that their combined output signal will properly identify different specific physical positions of the patient even if the overall sensor were to undergo a shift in its orientation after implantation in the patient's body.

It is desirable that the orientation of the sensors after implantation be such that one of them (sensor 13, in this example) is approximately horizontal and the other (here, sensor 12) approximately vertical when the patient is standing upright. In the exemplary configuration represented in FIG. 2, sensor 12 is somewhat smaller than and assembled within sensor 13 in the fixed relationship. In practice, the two position sensors may be separated, but nevertheless fixed in their orthogonal orientation. Under static motionless) conditions of either sensor of the pair, the mercury ball (not shown) is at rest and contacts specific ones among the set of electrodes (electrical contacts) 14 disposed about the side or floor of the sensor chamber. The electrodes are connected by respective electrical conductors to the output circuit of the sensor, each set of electrode locations in conductive contact identifying a particular position of the patient. As the patient changes position or engages in ongoing physical activity, one or both mercury balls will roll about within their respective chambers and make and break contact with the electrodes. The combined static locations of the mercury balls within the sensor pair, or their dynamic locations as they make and break connections between adjacent electrodes (closures and openings with time) is detected to provide information regarding the physical position, change in position, and ongoing movements of the patient.

In an alternative embodiment, the accelerometer may be piezoelectric, piezoresistive or piezocapacitive, fabricated in silicon or other semiconductor material within an integrated electronic or hybrid circuit, such as that described in U.S. Pat. No. 5,031,615. A hybrid semiconductor integrated circuit incorporates the accelerometer as a microminiature mechanoelectrical converter or transducer of high efficiency and low power consumption. This type of accelerometer 15, shown in FIG. 3, has a silicon monocrystalline substrate 15-1, an epitaxial doped layer 15-2 overlying the surface of substrate 15-1, and a polycrystalline silicon layer 15-3 sandwiched between passivating layers 15-4, 15-5 of silicon dioxide. A cavity 15-6 is formed in the substrate by etching, and portions of the silicon and passivating layers are removed by micromachining, forming a rectangular plate 15-7 connected by four arms to the corners of the cavity. The plate and its arms constitute the acceleration responsive element. An additional upper layer may be provided with an opening contiguous with the cavity to allow axial movement of plate 15-7 on its arms, and a protective layer of glass then disposed over the structure. An integrated circuit suitable for processing the movements of the plate in response to acceleration to provide the activity status signal may be fabricated in the silicon substrate, within the region generally below that designated by 15-8, by conventional semiconductor processing techniques.

FIG. 4 is a simplified diagram of an implantable medical interventional device such as a defibrillator 25 adapted to provide both antitachycardia and defibrillation therapies. The defibrillator includes batteries 27, electronics 29 (e.g., including a microprocessor 29-1, signal processing circuitry 29-2, sense amplifiers 29-3, memories 29-4, and other conventional components) and output capacitors 30 for storing electrical charge in variable quantities according to the amount of electrical energy to be delivered for shocking the heart to provide the desired therapy. The activity sensor is located within the defibrillator in the form, for example, of an accelerometer 34 with orthogonally oriented mercury ball sensors 35, 36 substantially as described in the text pertaining to FIG. 2, except that the two may be separately affixed to maintain that orientation. Accelerometer 34 is housed within but mechanically isolated from the case 32 which houses all of the other components of the defibrillator, to avoid sensitivity to pressure on the case. Alternatively, the sensor pair may be housed in its own biocompatible hermetically sealed case 38 for implantation in the patient in a location separate from the defibrillator case, as shown in phantom in the Figure.

The lead 40 for connecting the separately housed sensor implant 38 to the electronic control circuitry of the implanted defibrillator 25 may have a proximal end connector of a multiple contact type such as that disclosed in U.S. Pat. No. 4,971,057, to facilitate the signal processing. The defibrillator case 32 includes a header 43 with electrical connectors for the lead associated with the activity status sensor implant (if in a separate implantable case) and for the lead(s) connected to the defibrillating and other electrodes for delivering therapy and sensing cardiac activity. An ECG sense amplifier and related processing circuitry included within electronics 29 of the defibrillator provide an ECG signal (supplied in raw form from electrode(s) implanted on, in and/or adjacent the heart) for detecting rapid heart rates and other cardiac activity.

In operation, implantable defibrillator 25 is adapted to intervene upon detection of cardiac activity of the implant patient indicative of pathological VT or of VF by sequentially applying to the heart several different preprogrammed electrical waveforms conventionally utilized as protocols for treatment to break the VT or VF, as the case may be, while monitoring the patient's cardiac activity from the ECG signal following the application of each waveform. If the tachycardia continues or is accelerating, the protocol may be to successively employ more aggressive therapies. Therapy is ceased immediately upon detection that the treatment has been successful.

The activity status sensor detects physical activity and inactivity of the patient to complement detection of the patient's cardiac activity for confirming that a detected VT is a pathological tachycardia rather than a physiological tachycardia, if that be the case. The microprocessor in the device responds to such confirmation to select an appropriate one of the preprogrammed protocols stored in memory for treatment, with application of the selected electrical waveform to the heart via the output circuit of the device and the leads. In the example of the defibrillator, the shocks intended to defibrillate the heart are produced by charging the output capacitors of the device to the predetermined energy level, and then discharging them through the heart in the desired pulse and/or phased waveform, in a conventional manner.

The inability to fully assess the hemodynamic consequences of a tachycardia in different patients has frustrated previous attempts to provide a device universally adaptable to determine whether and when a particular antitachycardia therapy should be delivered. A particular patient may be able to tolerate an elevated heart rate of 180 bpm with a rapid decline of systolic blood pressure to 65, for example, while another patient, because of stenosis and weak cerebral profusion, may suffer loss of consciousness and respiratory functions with a tachycardia rate of 160 bpm and systolic blood pressure of 70. Measurements of heart rate, stroke volume, cardiac output, and even blood pressure do not fully delineate cerebral status for each individual patient. Hemodynamic parameters may appear to be within a normal range or not life-threatening, but they do not provide a true indication of the cerebral function of the patient.

The problem is exacerbated by the fact that in many individuals pathological tachycardia occurs at rates within the high end of the rate range which is normally reached when the patient is engaged in strenuous exercise, such as walking at a brisk pace. Despite the fact that the patient is ordinarily able to tolerate the elevated heart rate for at least short periods of exercise, the pathological tachycardia must be broken because it is not healthy for the heart to beat continuously at a rate of, say, 140 or 150 bpm, which is typical of this range, while the patient is at rest. Further, as noted earlier, the abnormal tachycardia may accelerate into fibrillation. Therefore, it is imperative that the device should provide an appropriate interventional therapy when this situation occurs, such as stimulation with low energy shocks to break the tachycardia.

If a conventional automatic implantable cardioverter and/or defibrillator were set at a tachycardia recognition rate of 150 bpm, for example, (and, as noted above, rate alone is the principal criterion, despite these devices using other characteristics of the ECG signal such as sudden onset or sudden rate change, rate stability, and so forth, as further indicia), the implant patient who reaches a heart rate of 152 bpm during exercise will be jolted with a stimulation of the heart. Depending on the specific protocol, the inappropriately applied therapy may cause the patient great discomfort and pain, possibly even loss of consciousness. If the same patient were to experience pathological VT of 140 bpm, therapy would not be applied at that time, and even though acceleration past a rate of 150 would then trigger a device response, time is of the essence since the order of difficulty in terminating the tachycardia increases with its longevity and possible progression into ventricular fibrillation. Hence, the patient may suffer very serious consequences.

Using an output provided by a non-ECG sensor to additionally indicate whether the patient is active or inactive when the tachycardia occurs, as in the device and method of the '092 application, helps significantly to better discriminate between physiological and pathological tachycardia. By comparing the ECG signal with the activity status signal, the occurrence of a slow pathological tachycardia can be recognized by the fact that the elevated heart rate is present with little or no physical activity by the patient, as distinguished from a physiological tachycardia where coincidence of rapid heart rate and pronounced physical activity is evident from the outputs of the two types of sensors. Nevertheless, it is not a complete answer because a threshold rate, or tachycardia recognition rate, is still desirable as a basis for comparison.

In the solution provided by the present invention, this threshold rate of the ECG criteria is adjusted according to the output of the non-ECG sensor, which here, as in the '092 application, is preferably an accelerometer. By observing the processed accelerometer signal, the activity status of the patient is determined, i.e., inactivity, moderate activity, strenuous activity, even the position of the patient. This information is then used to adjust the threshold rate—the tachycardia recognition criterion of the ECG. In its simplest form, the invention changes this rate from a first lower rate to a second higher rate, or vice versa, or simply leaves the existing rate setting in place, according to the status of the output signal of the accelerometer or other non-ECG sensor. In other words, the cardioverter/defibrillator (for example) in which the invention is implemented simply shifts the ECG tachycardia recognition rate upward and downward selectively according to the status of the non-ECG sensor output.

If the accelerometer output signal indicates that the patient is at rest, an appropriate threshold rate (the first lower rate) of 150 bpm might be selected because it is unlikely (to the point of being virtually nil) that emotional stress, fever or other physiological event than exercise, which is known to be absent here because of the status of the accelerometer output signal, would produce an elevated heart rate of such magnitude. Consequently, anything above this selected (programmed) threshold rate concurrent with such accelerometer output signal is recognized as a pathological tachycardia. On the other hand, if the accelerometer output subsequently indicates that the patient is physically active, the microprocessor of the device shifts the threshold rate upward to the second higher rate, such as 150 or even 170 bpm, so the patient may continue to engage in the exercise with consequent increased heart rate, but without the possibility of being subjected to shocks from the device unless the higher rate is exceeded. Here again, this higher threshold rate is carefully selected to exceed the maximum heart rate that the particular patient in which the device is to be implanted is likely to have while undergoing strenuous exercise.

In a method for quickly and discriminately recognizing pathological tachycardia so that electrical therapy will be delivered promptly to the heart of the cardiac patient to break the tachycardia, the recognition criteria provided by the patient's ECG are modified according to the status of a non-ECG sensor output signal indicative of the nature and extent of the patient's physical activity or lack of activity. The basic criterion of heart rate threshold is shifted to higher values with commencement and any subsequent increases of physical activity, and is shifted back to lower values with decreases and ultimate cessation of physical activity.

In a somewhat more complex embodiment and method, the electrical therapy of the implanted medical interventional device is tiered so that rate zones of ECG tachycardia recognition and consequent electrical therapies are shifted up or down under the control of the output of the non-ECG sensor. Thus, for example, before patient activity commences, the therapy protocols are bounded at the low end by that therapy associated with a recognized tachycardia exceeding the threshold rate for a rest output signal of the accelerometer. When activity commences, the entire rate zone or range is shifted upward to be bounded at the low end by a moderate threshold rate associated with the low activity output signal of the accelerometer. At that point, the lowest level of therapy (e.g., least aggressive therapy) for a tachycardia exceeding that moderate threshold rate is the least available therapy protocol as long as the tachycardia continues. There will be no return to the lower levels of therapy which were available in the zone having the lowest threshold rate. The same considerations apply as the activity becomes more strenuous, and a higher strenuous activity rate is set as the threshold, with the result that treatment will be limited to the still more aggressive therapies for a pathological tachycardia recognized in this zone associated with a non-ECG sensor output which indicates a magnitude indicative of strenuous activity level (exercise workload).

Figure 5:
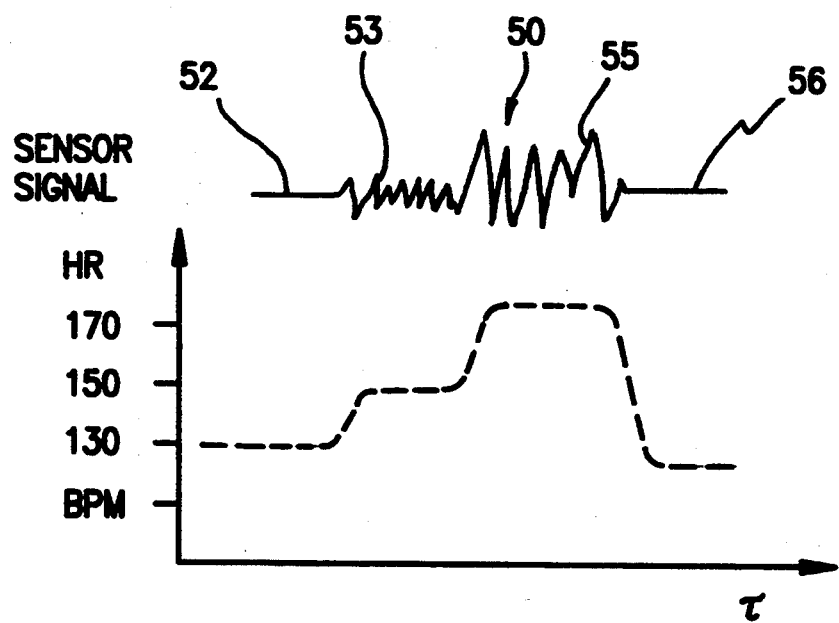
FIG. 5 is a graph of heart rate versus the relative to intervals of patient rest and exercise, illustrating the concepts of the present invention for shifting the ECG tachycardia recognition rate or entire zone of rates up or down under the control of the non-ECG sensor output.

These concepts are illustrated in the graph of FIG. 5, relating heart rate (HR) to time ($\tau$) for a portion of the output signal 50 of accelerometer 34 over the time interval of interest. In the period of patient rest designated as region 52 of output signal 50, the microprocessor in electronics system 29 of defibrillator 25 is programmed to set the ECG tachycardia recognition rate to 130 bpm. Thus, anything above that relatively low threshold rate (low, owing to the patient's state of rest) is considered to be a tachycardia for which the electrical therapy of the device will be administered to the patient's heart. In region 53 the patient has become active at a moderate activity rate as exhibited by the magnitude of the accelerometer sensor signal, and the microprocessor has responded to this signal by shifting the threshold rate to 150 bpm in accordance with the programming for that level of the sensor signal. This means, of course, that the patient would not be subjected to shocking by the device if his heart rate were to increase to say, 132, because the device has recognized through level detection or other conventional means the existence of activity from the non-ECG sensor output signal necessitating raising the threshold rate.

Subsequently, in region 55 the patient is engaging in more strenuous activity which results in another ramping up of the threshold rate, to 170 bpm in this example. At this point, although the patient's heart rate may be unlikely to reach that level as a consequence of exercise, so too, the margin of safety makes it highly unlikely that he will be subjected to the more aggressive therapy which would be appropriate for a tachycardia rate exceeding 170 bpm, from the exercise alone. Finally, region 56 of the accelerometer output signal indicates that the patient has returned to a state of resting, and the microprocessor therefore drops the threshold rate for tachycardia recognition back to 130 bpm.

Tiering of the electrical therapy of defibrillator 25 is accomplished by shifting entire rate zones of the ECG tachycardia recognition and their related electrical therapies upwardly or downwardly based on the output of the non-ECG sensor. In the graph of FIG. 5, for example, a first rate zone is programmed to exist for the patient at rest, when the output of the non-ECG sensor is at or very near zero. In this and every other zone, the threshold rate is the programmed lower boundary rate of the zone—here, 130 bpm. Thus, in regions 52 and 56 of the time interval of interest for output signal 50, a detected ECG heart rate anywhere in the zone above 130 bpm when the output signal of accelerometer 34 reflects patient resting, is recognized as pathological tachycardia and produces a response under the control of microprocessor 29-1 to deliver a basket of therapy protocols in preprogrammed sequence for as long as the pathological tachycardia remains unbroken. ECG cardiac activity is sensed after each therapy is delivered, to assess whether the tachycardia has been broken. As patient activity commences and subsequently becomes more strenuous, the entire rate zone or range is successively shifted upward to be limited by the moderate activity threshold rate and then the higher strenuous activity threshold rate, and so on. The result is that successively more aggressive therapies become the least available therapies in their respective rate zones as the output signal of the accelerometer indicates increasing activity by the patient.

The non-ECG sensor may be any type of known sensor, such as a single accelerometer, or two accelerometers as are depicted in FIGS. 2 and 4, indicative of acceleration and hence activity of the patient; a force sensor indicative for example of movements or pedal impacts and hence activity of the patient; an impedance sensor for measuring chest impedance of the patient with ventilation; a blood flow sensor; a blood pressure sensor; a blood oxygen sensor for measuring oxygen content or saturation; a blood temperature sensor for measuring changes in central venous temperature; a respiration sensor; a minute ventilation sensor; or other sensor characterized by utilization for rate-responsive pacing, including sensors not yet developed, where the parameter being detected is indicative of or provides additional information on the exercise or activity status of the patient.

An accelerometer is preferred for the sake of simplicity, rapid detection and reliability. For example, an accelerometer can be located readily within the device case, as in the preferred embodiment of FIG. 4, whereas other types of sensors such as those mentioned above generally require much more elaborate positioning not only outside the case but in locations requiring special surgical techniques for implantation in the patient. Further, an accelerometer does not utilize or require the type of complex technology typically associated with most other sensors such as those exemplified above, nor have the problems of long term instability, of drift, of decreased sensitivity in certain stages which characterize these other sensors. Additionally, an accelerometer is capable of detecting any kind of physical activity, and if two accelerometers are disposed at 90 degrees to one another as in FIG. 2, even the position of the patient may be detected, e.g., whether he is lying on his back, lying on his stomach, standing, falling or undergoing some other sudden change in position, and so forth.

Figure 6:
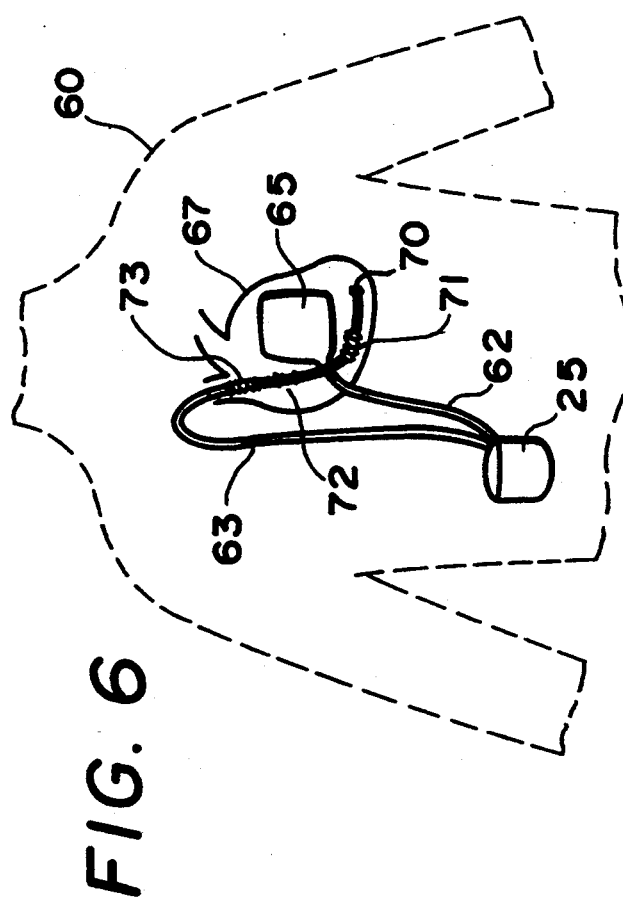
FIG. 6 is a phantom view of a patient having an implanted medical interventional device adapted to provide such threshold rate or zone shifting according to the invention, together with an implanted multi-electrode lead.

FIG. 6 illustrates defibrillator 25 implanted in a patient 60, with lead/electrode assemblies 62, 63 for epicardial patch electrode 65 and an endocardial counter-electrode 71, respectively. The patch electrode overlies an appropriate region of the epicardium and the counter-electrode in positioned in the right ventricle, for efficient delivery of the high voltage, high energy shock waveform to the heart 67. These or associated electrodes may be used to sense and monitor the patient's ECG and to deliver stimuli (pulses or higher level shocks) to the heart. Implantable defibrillation apparatus of various types is known in the art, and the specific type and location of the electrodes is not critical to an understanding of the present invention.

Transvenous lead 63 is preferably of the multi-conductor electrode type to facilitate and enable detection of signals as well as to deliver electrical stimulation at multiple locations within the patient's heart. For example, electrode tip 70 is positioned, when the lead is properly implanted, to be in direct contact with the myocardium in the right ventricle, and provide ventricular ECG status. Other relatively large sized electrode surfaces 71, 72, 73 and so forth on this lead are used for atrial and ventricular cardioversion or defibrillation and for bipolar sensing or conventional bipolar pacing according to device functions and patient requirements at any given time. For example, electrode surface 71 is a coil counter-electrode arranged to be positioned in the right ventricle for ventricular defibrillation, while electrode 73 is of similar configuration adapted to be positioned in or near the vena cava, when the lead is seated.

Floating electrode points 72 are bipolar electrodes integrated in the lead so as to be positioned in the right atrium when the lead is properly implanted. The atrial electrodes detect the electrical ECG and mechanical status of the atrium independent of the ventricular signal, so that the status of the atrial chamber is known in relation to the status of the ventricular chamber. Such ECG information in, proves the capability of the implanted device to discriminate between cardiac events in the ventricles such as sinus rate, sinus tachycardia, ventricular tachycardia with retrograde block, and others which are of primary ventricular origin, from those which are of primary atrial origin. For example, atrial dysrhythmias such as atrial tachycardia, atrial flutter or atrial fibrillation may be the primary and underlying cause for a secondary ventricular tachycardia. Accordingly, the ECG signals obtained from sensing electrodes in the atrium and the ventricle provide valuable information regarding the origin of a rhythm disorder of interest, and the type of therapy from among the therapies available from the device which are most likely to overcome the disorder and return the heart to normal sinus rhythm for the current physiological conditions.

Suitable floating electrode signal leads are known from VDD pacing principles, and are described, for example, by Brownlee in *PACE*, vol. 12 (March 1989), pp. 431–438, and by Heinz et al. in U.S. Pat. No. 5,078,133.

In the implanted device 25, the microprocessor evaluates the information obtained from the various sensors and applies the selected recognition criteria to distinguish between physiological and pathological tachycardia, with the interest being in the presence of ventricular tachycardia for reasons mentioned earlier herein. However, it may be that the VT is secondary, with the primary origin in the atrium. This state of affairs is not evident from the complementary sensor such as the activity sensor, which, if a pathological tachycardia is present, will simply indicates either that the patient is resting or is engaged in mild physical activity. If this state of affairs were all that is available, the device 25 capacitors would be charged and fired to deliver the appropriate cardioverting or defibrillating therapy to the ventricles. The result would be an inappropriate firing because such secondary VT is attributable to a primary AT here, and the selected therapy as well as its point of application would not suffice to break the tachycardia.

In this case, however, the microprocessor 29-1 also has the benefit of the atrial ECG status information derived from the atrial bipolar electrode for use in the evaluation, independent of the ventricular ECG status. Since this information from the atrium indicates the presence of AT, the evaluation performed by the microprocessor may be programmed in those circumstances to attribute the VT to primary atrial origin. Thus, the response is substantially immediate selection by the microprocessor of a therapy regimen to terminate the atrial tachycardia or fibrillation which led to the VT. An appropriate therapy, then, where atrial fibrillation is determined by evaluation of the sense signals to be the primary cause of a secondary VT, is to deliver low energy shocks, such as in a range from 0.25 to 1.0 joule, from device 25 to the myocardium of the atrial chambers, via one of the two poles of the bipolar sensing electrode(s) 72 disposed in the right atrium and the external patch or the vena cava counter-electrode. A tiered therapy regimen may be employed here, with the predetermined therapies selected to treat atrial dysrhythmias such as atrial flutter, tachycardia or fibrillation. In any event, the selected therapy is strictly or solely a response to an atrial event, such as the application of atrial defibrillation, and to avoid applying high energy shocks to the ventricles.

Moreover, where VT is present when AF is detected, irrespective of the output signal derived from the activity sensor (or other non-ECG sensor), it may be, and typically would be desirable to disable further shifting of the tachycardia recognition criteria, at least until the AF has been terminated. The reason for this is that the modification of recognition criteria is not particularly helpful in these circumstances, and may simply produce undesirable complexities for the analysis.

Figure 7:
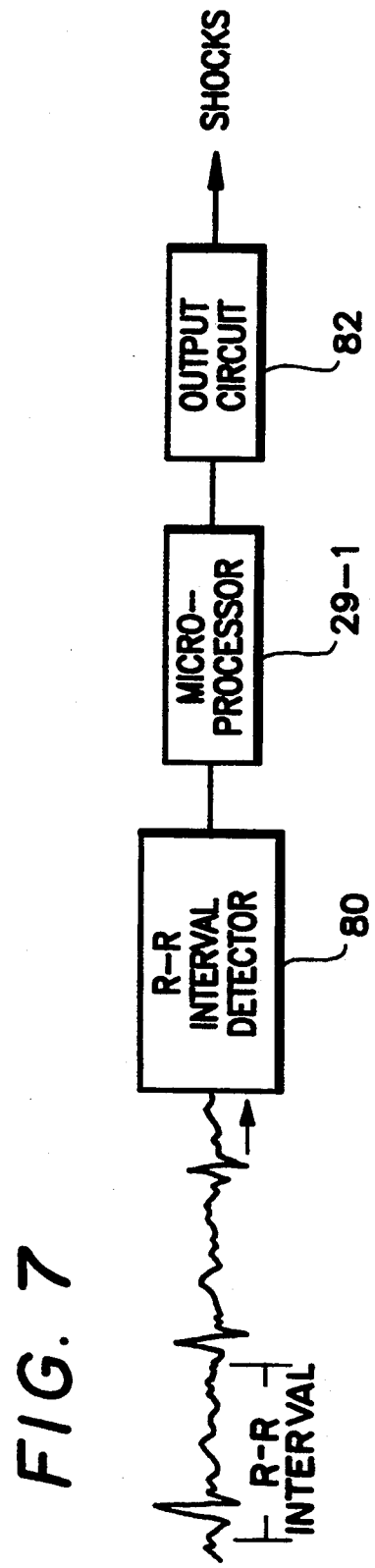
FIG. 7 is a block diagram of circuitry used for evaluation of a selected portion of the electrical cardiac activity of the patient according to another aspect of the invention.

With reference to FIG. 7, according to a related aspect of the invention, when a VT is detected the R-R interval, which is the coupling interval between heartbeats, is monitored by R-R interval detector 80. The purpose is to evaluate the ventricular EGG signals to determine whether the tachycardia exhibits a regular albeit rapid beat, or undergoes a variation in the R-R intervals. The output signal of the R-R detector 80, which representative of this is applied to microprocessor 29-1. If an R-R interval variation is occurring, it is an indication that an atrial dysrhythmia is present. In that event, the therapy should be applied in a manner to terminate the atrial dysrhythmia. The reason is that such a therapy will eliminate the VT because the atrial problem is primary, while the VT is only secondary. Here, this is achieved in the same manner as described above where an atrial dysrhythmia was found to be primary. The microprocessor controls the capacitors in output circuit 82 of device 25 to deliver low energy shocks in the range from about 0.25 to about 1.0 joule to the atrial chambers. As before, this is accomplished through one of the two poles 72 of the bipolar atrial sensing electrode(s) and the patch or counter-electrode. A tiered therapy regimen may be employed here also.

In contrast, an attempt to terminate such a secondary VT directly, by application of high voltage shocks through the ventricles, would prove unsuccessful in addition to causing sever trauma to the patient and a marked reduction in battery life.

When atrial dysrhythmia is found to be the primary cause of the VT, it becomes undesirable to attempt to modify the tachycardia recognition rate as was described earlier herein. Such modification of criteria is used for the specific purpose of providing more reliable detection of VT when the patient appears to be engaged in exercise. However, when an irregular R-R interval is detected it is clear that exercise is not taking place. Accordingly, the modification response to the activity sensor output is disabled by the microprocessor when a variation in the R-R interval is detected while a VT is occurring.

Although certain preferred embodiments and methods have been disclosed herein, it will be apparent to those skilled in the art from a consideration of the foregoing description that variations and modifications of the described embodiments and methods may be made without departing from the true spirit and scope of the invention. Accordingly, it is intended that the invention shall be limited only to the extent required by the appended claims and the rules and principles of applicable law.

What is claimed is:

1. An implantable medical interventional device for delivering electrical therapies to the heart of an implant patient to treat pathologic ventricular tachycardia, comprising:

first sensor means adapted to generate a signal indicative of the patient's ventricular ECG status, second sensor means adapted to generate a signal indicative of the patient's atrial ECG status, evaluation means for establishing criteria to distinguish physiologic and pathologic tachycardias in the ventricles from an evaluation of the signal generated by said first sensor means and adapted to apply an appropriate therapy in response to an evaluation that a pathologic tachycardia is present, said evaluation means including therapy delivering means responsive to the signal generated by said second sensor means indicative of atrial fibrillation or other atrial dysrhythmias for limiting the therapy to an atrial response.

2. The device of claim 1, in which:

the evaluation means is further adapted to compare the signals indicative of atrial ECG status and ventricular ECG status to discriminate primary ventricular tachycardias from secondary ventricular tachycardias of primary atrial origin, and the therapy delivering means is adapted to deliver electrical therapies in a tiered regimen and is responsive to said discrimination of primary and secondary ventricular tachycardia to adjust the tiered therapy regimen accordingly.

3. The device of claim 2, in which:

the tiered therapy regimen includes a therapy of solely atrial defibrillation.

4. The device of claim 1, further including:

a non-EGG sensor adapted to sense a physiological parameter indicative of patient activity.

5. The device of claim 4, in which:

the evaluation means is responsive to detection of atrial fibrillation or other atrial dysrhythmia by the second sensor means, detection of ventricular tachycardia by the first sensor means, and an indication of a resting condition or low level activity by the non-ECG sensor, to treat the ventricular tachycardia as pathologic atrial tachycardia, and to select atrial defibrillation as the therapy to be applied, without delivery of any therapy to the ventricle.

6. The method of controlling pathologic tachycardia whether in the atrium or the ventricles of the heart, including:

sensing atrial and ventricular dysrhythmias, providing tiered electrical therapies for application to the heart to treat the sensed dysrhythmia, and responding to a sensed ventricular dysrhythmia in the right ventricle and to a sensed atrial dysrhythmia in the right atrium while the patient is substantially at rest, by treating both the ventricular dysrhythmia and the atrial dysrhythmia with one of the tiered therapies applied solely to the atrium.

7. The method of claim 6, in which:

the tiered therapy applied solely to the atrium is defibrillation therapy applied to one of the two atrial poles used for bipolar sensing of the atrial ECG.

8. The method of claim 7, wherein:

evaluation of the ECG signal includes using signal information indicative of both the ventricular ECG status and the atrial ECG status.

9. The method of claim 8, wherein:

one of the therapies among the tired electrical therapies which may be selected is solely atrial defibrillation without a concurrent therapy applied to the ventricles.

10. An implantable medical interventional device for delivering electrical therapies to the heart of an implant patient to treat pathologic ventricular tachycardia, comprising:

first sensor means adapted to be positioned in the patient's right ventricle to sense ventricular electrical activity, second sensor means adapted to be positioned in the patient's right atrium to sense atrial electrical activity, and defibrillation electrode means adapted to be positioned in the patient's right ventricle to electrically stimulate excitable myocardial tissue thereof;

evaluation means establishing criteria to distinguish ventricular tachycardia of physiologic origin and of pathologic origin, and responsive to said first and second sensor means for determining whether a pathologic ventricular tachycardia is primary, originating from ventricular dysfunction, or secondary, originating from atrial dysfunction; and control means responsive to said evaluation means for selecting an electrical therapy for delivery to the patient's heart;

all of said first and second sensor means and said defibrillation electrode means being disposed on the same electrode structure.

11. The device of claim 10, including:

another defibrillation electrode means adapted to be positioned in the patient's right atrium to electrically stimulate excitable myocardial tissue thereof, on said same electrode structure.

12. The device of claim 11, wherein:

said another defibrillation electrode means is part of said second sensor means.

13. A method of controlling both atrial and ventricular pathologic dysrhythmias, including:

sensing atrial and ventricular dysrhythmias utilizing respective recognition criteria, normally modifying the recognition criteria for ventricular dysrhythmias if it is determined that the patient is undergoing exercise and removing the modification when the patient returns to a state of rest, providing tiered electrical therapies for application to the heart to treat the sensed dysrhythmia, responding to a sensed dysrhythmia in the fight ventricle and to a sensed atrial dysrhythmia in the right atrium as indicative that the atrial dysrhythmia is primary, by treating both the ventricular dysrhythmia and the atrial dysrhythmia with one of the tiered therapies applied solely to the atrium, while avoiding modification of the recognition criteria.

14. The method of claim 13, in which:
the step of applying a tiered therapy solely to the atrium is performed by applying a cardioversion therapy applied to an atrial electrode which is also used for sensing the atrial ECG.

15. The method of claim 13, wherein:
the dysrhythmia in the right ventricle is sensed by detecting the R-R interval of the patient's electrical cardiac activity.

16. The method of claim 15, wherein:
determination that the ventricular dysrhythmia is arising from atrial dysrhythmia is made upon sensing an irregular R-R interval.

* * * * *